United States Patent [19]

Jonas et al.

[11] 4,171,370
[45] Oct. 16, 1979

[54] PHENOXY-AMINO-PROPANOLS

[75] Inventors: Rochus Jonas; Karl-Heinz Becker; Hans-Joachim Enenkel; Klaus Minck; Hans-Jochen Schliep, all of Darmstadt, Fed. Rep. of Germany

[73] Assignee: Merck Patent Gesellschaft mit beschränkter Haftung, Darmstadt, Fed. Rep. of Germany

[21] Appl. No.: 839,487

[22] Filed: Oct. 4, 1977

[30] Foreign Application Priority Data

Oct. 9, 1976 [DE] Fed. Rep. of Germany ....... 2645710

[51] Int. Cl.² .................. A61K 31/36; A61K 31/135; C07D 317/06
[52] U.S. Cl. .............................. 424/282; 260/340.5 R; 424/330
[58] Field of Search .................. 424/282; 260/340.5 R

[56] References Cited

U.S. PATENT DOCUMENTS

| | | | |
|---|---|---|---|
| 3,644,469 | 2/1972 | Köppe et al. .......................... | 424/282 |
| 3,732,253 | 5/1973 | Cavalleri et al. .............. | 260/240.5 R |
| 3,966,770 | 6/1976 | Kaiser et al. .......................... | 424/282 |
| 4,067,904 | 1/1978 | Comer et al. ......................... | 424/282 |

*Primary Examiner*—Allen J. Robinson
*Attorney, Agent, or Firm*—Millen & White

[57] ABSTRACT

New phenoxy-amino-propanols of formula

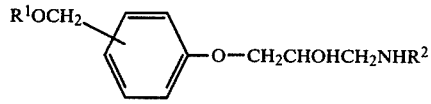

wherein R¹ is alkenyl, alkynyl, alkoxyalkyl or alkenyloxyalkyl with 2–6 C atoms in each case or cycloalkyl with 3–8 C atoms; and R² is alkyl or hydroxyalkyl with 1–6 C atoms in each case, cycloalkyl with 3–8 C atoms, aralkyl or aralkyl wherein the aryl radical is mono- to tri-substituted by alkyl, alkoxy, OH, F and/or Cl or mono-substituted by methylenedioxy, with a total of 7–15 C atoms in each case, and the physiologically acceptable acid addition salts thereof, exhibit various pharmacological properties including isoprenaline-antagonism on the heart rate and blood pressure.

6 Claims, No Drawings

PHENOXY-AMINO-PROPANOLS

SUMMARY OF THE INVENTION

This invention relates to new compounds and their physiologically acceptable salts.

In a composition aspect, this invention relates to compounds having the formula

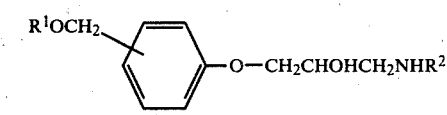

wherein $R^1$ is alkenyl, alkynyl, alkoxyalkyl or alkenyloxyalkyl with 2–6 C atoms in each case or cycloalkyl with 3–8 C atoms; and $R^2$ is alkyl or hydroxyalkyl with 1–6 C atoms in each case, cycloalkyl with 3–8 C atoms or aralkyl or aralkyl wherein the aryl radical is mono- or tri-substituted by alkyl, alkoxy, OH, F, Cl or combinations thereof or mono-substituted by methylenedioxy, with a total of 7–15 C atoms in each case.

In another composition aspect, this invention relates to compositions containing the compounds for Formula I and pharmaceutically acceptable carriers.

In a method of use aspect, this invention relates to a method for obtaining pharmaceutical effects including isoprenaline-antagonism on the heart rate and blood pressure, which comprises administering a pharmaceutically effective amount of a compound of Formula I.

DETAILED DISCUSSION

In Formula I, the group $R^1OCH_2$— is preferably in the p- or o-position of the benzene ring; however, it can also be in the m-position.

When the radical $R^1$ is alkenyl, it is preferably straight-chained. Suitable radicals include allyl, vinyl, propenyl, isopropenyl, butenyl (for example, but-1-en-1-yl, but-1-en-2-yl, but-2-en-1-yl, but-2-en-2-yl, but-3-en-1-yl and but-3-en-2-yl), isobutenyl (for example 2-methyl-prop-2-en-1-yl), pentenyl (for example pent-2-en-1-yl) or hexenyl (for example hex-2-en-1-yl). Allyl is particularly preferred. The alkynyl groups are also preferably straight-chained and include propargyl, ethynyl, prop-1-yn-1-yl, butynyl (for example but-2-yn-1-yl), pentynyl (for example pent-2-yn-1-yl) or hexynyl (for example hex-2-yn-1-yl). Propargyl is particularly preferred. Alkoxy-alkyl groups are also preferably straight-chained, preferably alkoxyethyl (wherein the alkoxy group has 1–4 C atoms), in particular 2-methoxyethyl, 2-ethoxyethyl, 2-propoxyethyl or 2-isopropoxyethyl. Other suitable alkoxyalkyl groups include alkoxy-propyl, for example 2- or 3-methoxypropyl; alkoxybutyl, for example 2-, 3- or 4-methoxybutyl; and alkoxypentyl, for example 5-methoxypentyl. Alkenyloxyalkyl groups are preferably 2-alkenyloxyethyl and in particular 2-allyloxyethyl. Other suitable such groups include 2-vinyloxyethyl or 2-propenyloxyethyl, and also, for example, alkenyloxypropyl, such as 2- or 3-allyloxypropyl. Cycloalkyl groups are preferably cyclopentyl or cyclohexyl; but other suitable cycloalkyl groups include cyclopropyl, cyclobutyl, 1-, 2- or 3-methylcyclopentyl, 1-, 2-, 3- or 4-methylcyclohexyl, cycloheptyl and cyclooctyl.

When the radical $R^2$ is alkyl, it is preferably branched alkyl, in particular with 3 or 4 C atoms, such as isopropyl, isobutyl or tert-butyl. Other suitable alkyl groups include methyl, ethyl, n-propyl, n-butyl, sec-butyl, pentyl, such as 1-, 2- or 3-pentyl, isopentyl, neopentyl, tert-pentyl, hexyl, such as 1-, 2- or 3-hexyl and isohexyl. Suitable hydroxyalkyls include for example: hydroxymethyl, 1- or 2-hydroxyethyl, 1-, 2- or 3-hydroxypropyl, 1-hydroxy-1-methyl-ethyl, 1-methyl-2-hydroxyethyl, 1-, 2-, 3- or 4-hydroxybutyl, 5-hydroxypentyl and 6-hydroxyhexyl. When $R^2$ is cycloalkyl, suitable groups are those indicated above for $R^1$.

When $R^2$ is aralkyl, it has 7–15, preferably 7–11 C atoms. The aryl group is a hydrocarbon. The preferred aralkyl is 2-phenylethyl. Other suitable groups include benzyl, 1-phenylethyl, 1-methyl-2-phenylethyl, 1,1-dimethyl-2-phenylethyl, 2-methyl-2-phenylethyl, 2,2-dimethyl-2-phenylethyl, 1,2-dimethyl-2-phenylethyl, 1-, 2- or 3-phenylpropyl, 1-methyl-3-phenylpropyl, 1-, 2-, 3- or 4-phenylbutyl, 1- or 2-naphthylmethyl, 2-(1-naphthyl)-ethyl or 2-(2-naphthyl)-ethyl. The alkyl group of the aralkyl preferably has from 1 to 4 C atoms.

The aryl radical of the aralkyl group can also be mono- to tri-substituted by alkyl, alkoxy, OH, F and/or Cl or monosubstituted by methylenedioxy. Suitable alkyl or alkoxy substituent groups have 1–8, preferably 1–4 C atoms. However, per above, the substituted aralkyl radical may not contain more than a total of 15 C atoms, preferably 7–11 C atoms. Suitable alkyl groups include in particular, methyl, ethyl, n-propyl, isopropyl, n-butyl, isobutyl, sec-butyl, tert-butyl, n-pentyl, isopentyl, n-hexyl, n-heptyl and n-octyl. Suitable alkoxy groups include in particular, methoxy, and also ethoxy, n-propoxy, isopropoxy, n-butoxy, isobutoxy, sec-butoxy, tert-butoxy, n-pentyloxy, isopentyloxy, n-hexyloxy, n-heptyloxy and n-octyloxy.

The most preferred substituted aryl radicals are, alkoxyphenyl groups, such as o-, m- or p-methoxyphenyl; or o-, m- or p-ethoxyphenyl; dialkoxyphenyl, such as 2,3-, 2,4-, 2,5-, 2,6-, 3,5- or, particularly preferably 3,4-dimethoxyphenyl; trialkoxyphenyl, such as 3,4,5-trimethoxyphenyl; methylenedioxyphenyl, such as 3,4-methylenedioxyphenyl. Also preferred are for example, alkylphenyl, such as o-, m- or p-tolyl, o-, m- or p-ethylphenyl, o-, m- or p-isopropylphenyl or o-, m- or p-tert-butylphenyl; dialkylphenyl, such as 2,3-, 2,4-, 2,5-, 2,6-, 3,4- or 3,5-dimethylphenyl; trialkylphenyl, such as 2,4,6-trimethyl-phenyl or 2,6-dimethyl-4-tert-butylphenyl; o-, m- or p-hydroxyphenyl; dihydroxyphenyl, such as 3,4-dihydroxyphenyl; o-, m- or p-fluorophenyl and o-, m- or p-chlorophenyl. The aryl radicals can also carry two different substituents, such as 3-methoxy-4-hydroxyphenyl and 3-hydroxy-4-methoxyphenyl. 2-(3,4-dimethoxyphenyl)-ethyl is a particularly preferred substituted aralkyl radical. Further particularly preferred substituted aralkyl radicals are, for example, 2-(p-methoxyphenyl)-ethyl, 2-(3,4,5-trimethoxyphenyl)-ethyl and 2-(3,4-methylenedioxyphenyl)-ethyl.

This invention accordingly relates, in particular, to those compounds of Formula I in which at least one of the radicals $R^1$ and $R^2$ has one of the preferred meanings indicated above.

Contemplated classes of compounds within the scope of Formula I are those wherein:
(a) $R^1$ is alkenyl;
(b) $R^1$ is alkynyl;
(c) $R^1$ is alkoxyalkyl;
(d) $R^1$ is alkenyloxyalkyl;
(e) $R^1$ is cycloalkyl;
(f) $R^2$ is alkyl including each of (a)–(e);
(g) $R^2$ is hydroxyalkyl including each of (a)–(e);

(h) R² is cycloalkyl including each of (a)–(e);
(i) R² is aralkyl including each of (a)–(e);
(j) R² is substituted aralkyl including each of (a)–(e);
(k) R² is substituted aralkyl wherein the substituent is OH or alkoxy including each of (a)–(e);
(l) R² is substituted aralkyl wherein the substituent is F or Cl including each of (a)–(e);
(m) R² is substituted aralkyl wherein the substituent is methylenedioxy including each of (a)–(e); and
(n) R² is substituted aralkyl wherein the substituent is alkyl including each of (a)–(e).

Some preferred groups of compounds can be expressed by the following partial Formulae Ia to Ip which correspond to the Formula I and wherein the radicals not described in more detail are as defined for Formula I, but wherein in Ia, R¹ is alkenyl or alkynyl with 2–6 C atoms in each case;
in Ib, R¹ is alkoxyalkyl or alkenyloxyalkyl with 2–6 C atoms in each case;
in Ic, R¹ is cycloalkyl with 3–8 C atoms;
in Id, R¹ is allyl, propargyl, 2-alkoxyethyl with 3–5 C atoms, 2-allyloxyethyl or cyclopentyl;
in Ie, R² is alkyl or hydroxyalkyl with 1–6 C atoms in each case or cycloalkyl with 3–8 C atoms;
in If, R² is unsubstituted aralkyl or aralkyl wherein the aryl radical is mono- or tri-substituted by alkyl, alkoxy, OH, F and/or Cl or is mono-substituted by methylenedioxy, with a total of 7–15 C atoms in each case;
in Ig, R² is isopropyl, tert-butyl, 2-phenylethyl, 1,1-dimethyl-2-phenylethyl or 2-(3,4-dimethoxyphenyl)-ethyl;
in Ih, R² is isopropyl or tert-butyl;
in Ii, R² is 2-phenylethyl or 2-(3,4-dimethoxyphenyl)-ethyl;
in Ij, R¹ is alkenyl or alkynyl with 2–6 C atoms in each case and R² is alkyl with 1–6 C atoms, phenylalkyl with 7–10 C atoms or phenylalkyl wherein phenyl is mono- to tri-substituted by methoxy or mono-substituted by methylenedioxy, with a total of 9–13 C atoms;
in Ik, R¹ is allyl, propargyl, 2-alkoxyethyl with 3–5 C atoms, 2-allyloxyethyl or 2-cyclopentyl and R² is isopropyl, tert-butyl, 2-phenylethyl, 1,1-dimethyl-2-phenylethyl or 2-(3,4-dimethoxyphenyl)-ethyl;
in Il, R¹ is allyl or propargyl and R² is isopropyl, tert-butyl, 2-phenylethyl, 1,1-dimethyl-2-phenylethyl or 2-(3,4-dimethoxyphenyl)-ethyl;
in Im, R¹ is allyl or propargyl and R² is 2-(3,4-dimethoxyphenyl)-ethyl;
in In, R¹ is alkoxyalkyl or alkenyloxyalkyl with 2–6 C atoms in each case or cycloalkyl with 3–8 C atoms and R² is alkyl with 1–6 C atoms, phenylalkyl with 7–10 C atoms or phenylalkyl wherein phenyl is mono- to tri-substituted by methoxy or mono-substituted by methylenedioxy, with a total of 9–13 C atoms;
in Io, R¹ is 2-alkoxyethyl with 3–5 C atoms, 2-allyloxyethyl or cyclopentyl and R² is isopropyl, tert-butyl, 2-phenylethyl, 1,1-dimethyl-2-phenylethyl or 2-(3,4-dimethoxyphenyl)-ethyl; and
in Ip, R¹ is 2-alkoxyethyl with 3–5 C atoms or 2-allyloxyethyl and R² is isopropyl or tert-butyl.

The compounds of Formula I possess at least one asymmetric C atom and can contain further asymmetric C atoms in the substituents R¹ and R². They can thus exist in the racemic or in the optically active form. They are generally obtained as racemates in synthesis.

The compounds of Formula I can be prepared by conventional methods which are described in the literature, for example, in standard works such as Houben-Weyl, *Methoden der Organischen Chemie*, Georg-Thieme-Verlag, Stuttgart; and *Organic Reactions*, John Wiley and Sons, Inc., New York. Suitable reaction conditions are known and details can be determined by conventional considerations. Use can also be made of conventional variations which are not discussed in detail herein.

Such processes for the preparation of the phenoxyamino-propanols of Formula I and their physiologically acceptable acid addition salts, include:

(1) reacting a compound of Formula II

Ar—O—CH₂—CHQ—CH₂Y    II with a compound of Formula III

Z—R²    III wherein Ar is

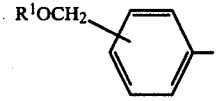

one of the radicals Y and Z is NH₂ and the other is X; Q is OH or, together with X, is an oxygen atom; X is Hal, OH, a functionally modified OH group or (in II), together with Q, is an oxygen atom; Hal is Cl, Br or I; and R¹ and R² are as defined above;

(2) reacting a phenol of Formula IV

Ar—OH    IV wherein Ar is as defined above, with an aminoalcohol of Formula V

X—CH₂CHOHCH₂NHR²    V wherein R² and X are as defined above;

(3) reacting a compound of Formula VI

Ar—O—CH₂—W    VI wherein W is a radical which can be reduced to the group —CHOH—CH₂—NHR² and Ar and R² are as defined above, with a reducing agent; and (4) treating a compound of the Formula I which, however, has one or more group(s) which can be split off solvolytically or hydrogenolytically in place of one or more of its H atoms, with a solvolyzing or hydrogenolyzing agent.

The physiologically acceptable acid addition salts are prepared by treating a resulting base of Formula I with an acid.

Some of the starting materials used in preparation of the compounds of Formula I are known and some are new. The new starting materials can be prepared by conventional processes in analogous manner to those used to prepare the known starting materials. If desired, the starting materials can also be formed in situ without being isolated from the reaction mixture but rather immediately reacted to produce the compounds of Formula I.

In the following text, the radicals $R^1$, $R^2$, Ar, Hal, Q, W, X, Y and Z are as defined for Formulae I to VI, unless otherwise expressly indicated.

The radical X can be present in the starting materials of Formulae II, III and V. X is preferably Cl or Br, but I, OH or a functionally modified OH group are also suitable. Suitable functionally modified OH groups, in particular, include reactive esterified OH groups, for example alkylsulphonyloxy preferably with 1–6 C atoms, such as methanesulphonyloxy, or arylsulphonyloxy preferably with 6–10 C atoms, such as benzenesulphonyloxy, p-toluenesulphonyloxy or 1- or 2-naphthalenesulphonyloxy.

In general, the starting materials of Formula II are new. They can be obtained, for example, by reacting phenols of the Formula Ar—OH (IV) with compounds of the Formula X—CH$_2$—CHQ—CH$_2$Y (for example epichlorohydrin or epibromohydrin). Primary amines of Formula II (Y=NH$_2$) can be prepared, for example, by reacting epoxides of Formula II (i.e., Q and Y are together an oxygen atom) with ammonia or with benzylamine and subsequently removing the benzyl group hydrogenolytically.

Generally, starting materials of Formula III are known. The Formula III amines (Z=NH$_2$) can be obtained from the corresponding halogen compounds of Formula III (Z=Hal) by reaction with ammonia or by reaction with benzylamine and subsequent hydrogenolytic splitting-off of the benzyl group. Compounds of the Formulae II and III in which the radicals Y or Z are functionally modified OH groups can be obtained by functional modification of the corresponding alcohols, for example by reaction with alkyl- or aryl-sulphonyl halides in the presence of pyridine.

Generally, the phenols of Formula IV are new. They can be obtained by reacting o-, m- or p-hydroxybenzyl alcohol with compounds of the formula $R^1$-X, preferably by etherification with the corresponding alcohols of the formula $R^1$—OH, which as a rule are known. Aminoalcohols of Formula V can be prepared, for example, by reacting compounds of the formula X—CH$_2$—CHQ—CH$_2$Y (preferably epoxides, such as epichlorohydrin) with amines of Formula III (Z=NH$_2$).

In the starting materials of Formula VI, the substituent W is a group which can be reduced to the group —CHOH—CH$_2$—NHR$^2$, preferably one of the groups —CO—CH$_2$—NHR$^2$ (=W$^1$), —CHOH—CH=NR$^2$ (=W$^2$), —CHOH—CH$_2$—N=R$^3$ (=W$^3$; wherein R$^3$ is an alkylidene, hydroxyalkylidene or cycloalkylidene group or an aralkylidene group which is unsubstituted or which has aryl substitution as indicated in the definition of R$^2$), or —CHOH—CH$_2$—NH—R$^4$ (=W$^4$; wherein R$^4$ is a radical which can be reduced to the group R$^2$, for example a radical corresponding to the group R$^2$ but which contains an additional C—C bond or an oxygen atom instead of two hydrogen atoms, for example alkanoyl, oxoalkyl, alkenyl, hydroxyalkanoyl or hydroxyalkenyl with up to 6 C atoms in each case, or oxocycloalkyl or cycloalkenyl with 3–8 C atoms or oxoarylalkanoyl, aryl-oxoalkyl or arylalkenyl, unsubstituted or having aryl groups substituted as indicated in the definition of R$^2$, with a total of 7–15 C atoms in each case).

The compounds of the Formula VI can be obtained, for example, by reacting the phenols of Formula IV with compounds of the formula X—CH$_2$—W. Furthermore, the starting materials of Formula VI (W=W$^1$) can be obtained by reacting compounds of the formula Ar—O—CH$_2$—CO—CH$_2$—X with amines of the formula R$^2$—NH$_2$; the compounds of the Formula VI (W=W$^2$) can be obtained by reacting aldehydes of the formula Ar—O—CH$_2$—CHOH—CHO with amines of the formula R$^2$—NH$_2$; the compounds of the Formula VI (W=W$^3$) can be obtained by reacting amines of the formula Ar—O—CH$_2$—CHOH—CH$_2$NH$_2$ with aldehydes of the formula R$^3$=O; and the compounds of the Formula VI (W=W$^4$) can be obtained by reacting compounds of the formula Ar—O—CH$_2$—CHOH—CH$_2$—X with amines of the formula R$^4$—NH$_2$.

The compounds of Formula I are preferably prepared by reacting compounds of Formula II with compounds of Formula III. On the one hand, it is possible to react epoxides of Formula II (Q and Y together are an oxygen atom), halogeno-alcohols of the Formula II (Q=OH, Y=Hal) or diols or their functional derivatives of the Formula II (Q=OH, Y=OH or functionally modified OH) with amines of the Formula III (Z=NH$_2$); and on the other hand it is possible to react amines of the Formula II (Q=OH, Y=NH$_2$) with compounds of the Formula III (Z=X). The reaction of the epoxides with amines of the formula R$^2$-NH$_2$ is preferred.

The reaction of compounds of Formula II with compounds of Formula III can be optionally carried out in the presence of an additional inert solvent, at temperatures between about 0° and 200° C., preferably between about 20° and 120° C. Suitable inert solvents are conventional for amination reactions of this type, and are known, from the literature, for example water; alcohols, such as methanol, ethanol, isopropanol or n-butanol; ethers, such as diethyl ether, diisopropyl ether, tetrahydrofuran (THF) or dioxane; hydrocarbons, such as benzene, toluene or xylene; halogenated hydrocarbons, such as dichloromethane, chloroform or trichloroethylene; nitriles, such as acetonitrile; amides, such as dimethylformamide (DMF); or sulphoxides, such as dimethylsulphoxide (DMSO). Mixtures of these solvents can also be used. The amines are preferably used in a molar ratio of at least 1:1 or in excess. If they are used in excess, they can simultaneously serve as the solvent. It is also possible to add an additional base, for example an inorganic base, such as sodium or potassium hydroxide, sodium carbonate, potassium carbonate, sodium bicarbonate or potassium bicarbonate. If the starting compounds have a structure such that one mole of acid is split off during the reaction (for example if halohydrins are used, so that hydrogen halide is split off), it is preferred to employ either an additional base or an excess of the amine.

If X is an OH group, or also an alkyl- or arylsulphonyloxy group, it may also be advisable to add an acid catalyst, for example an inorganic acid (such as sulphuric acid, polyphosphoric acid, hydrobromic acid or hydrochloric acid) and/or an organic acid (such as formic, acetic, propionic or p-toluenesulphonic acid). An excess of the acid can also simultaneously serve as the solvent.

The required reaction times are between about 10 minutes and 7 days, depending on the starting materials and the reaction temperature. It is also possible to carry out the process under pressure (up to about 200 atmospheres) and thereby accelerate the reaction.

The compounds of Formula I can also be obtained by reacting the phenols of Formula IV with the aminoalcohols of Formula V. Optionally, the phenol IV can first be converted into a salt, in particular a metal salt, for example an alkali metal salt (Li, Na or K salt). This can be accomplished by reacting the phenol with a reagent which forms metal salts, for example an alkali metal (e.g., Na), an alkali metal hydride or amide (for example, LiH or NaH or NaNH$_2$ or KNH$_2$), an alkali metal alcoholate (wherein the alcohol portion preferably has 1–4 C atoms, for example lithium methylate, ethylate or tert-butylate, sodium methylate, ethylate or tert-butylate or potassium methylate, ethylate or tert-butylate), an organometallic compound (for example, butyllithium, phenyllithium or phenylsodium) or a metal hydroxide, carbonate or bicarbonate (for example, of Li, Na, K or Ca). The preparation of the phenolate is advantageously carried out in the presence of a solvent or solvent mixture. Suitable solvents include, for example, hydrocarbons (such as hexane, benzene, toluene or xylene), ethers (for example, diethyl ether, diisopropyl ether, THF, dioxane or diethylene glycol dimethyl ether), amides (for example, DMF), alcohols (for example, methanol or ethanol) or ketones (for example, acetone or butanone). The phenol IV or its salt is preferably reacted with compound V in the presence of a diluent, for example, the solvent which has been used for the preparation of the salt, which, however, can be replaced by or diluted with another solvent. Generally, the reaction is carried out at temperatures between about −20° and 150° C., preferably between 20° and 120° C.

The phenolate can also be formed in situ. In this case, the phenol IV and compound V are allowed to react with one another in the presence of a base. A particularly preferred method is to heat the compounds IV and V together with an alcoholic-aqueous sodium hydroxide solution for about 5 to 15 hours.

Furthermore, it is possible to reduce a compound of Formula VI in order to prepare the compounds of Formula I. Suitable reducing agents include, for example, complex metal hydrides. The compounds of Formula VI can also be reduced with the aid of catalytically activated or nascent hydrogen. Among the complex metal hydrides, sodium borohydride and lithium aluminum hydride are preferred. The reaction is preferably carried out in one of the conventional solvents, with NaBH$_4$ preferably in an alcohol, such as methanol or ethanol, and with LiAlH$_4$ preferably in an ether, such as diethyl ether or di-n-butyl ether, THF or ethylene glycol dimethyl ether. Suitable reaction temperatures are generally between about −80° and 150° C., preferably between 15° C. and the boiling point of the solvent.

Suitable catalysts for the catalytic hydrogenation include, for example nickel and cobalt catalysts, and noble metal and mixed catalysts, such as copper/chromium oxide. The noble metal catalysts can be supported (for example platinum- or palladium-on-charcoal or palladium-on-calcium carbonate or -strontium carbonate), or be in the form of oxide catalysts (for example platinum oxide) or finely divided metal catalysts. Nickel and cobalt catalysts are preferably employed as Raney metals. Nickel can also be used on kieselghur or pumice supports.

The hydrogenation can be carried out at room temperature under normal pressure, or also at elevated temperature and/or under increased pressure. The reaction is preferably carried out under pressures between 1 and 100 atmospheres and at temperatures between −80° and +150° C., especially between room temperature and +100° C. The reaction is carried out in acidic, neutral or basic conditions and in the presence of a solvent, such as water, methanol, ethanol, isopropanol, n-butanol, ethyl acetate, dioxane, acetic acid or THF. Mixtures of these solvents can also be used. Raney metals are preferred catalysts for the catalytic hydrogenation of the aminoketones of Formula VI (W=W$^1$).

If nascent hydrogen is used as the reducing agent, it can be produced, for example, by treating metals with acids or bases. For example, mixtures of zinc and acid or alkali metal hydroxide solution; of iron and hydrochloric acid or acetic acid; or of tin and hydrochloric acid can be used. The use of sodium or another alkali metal in an alcohol, such as ethanol, isopropanol, butanol or amyl or isoamyl alcohol, or phenol is also suitable. Furthermore, an aluminum/nickel alloy in an alkaline-aqueous solution, optionally with the addition of ethanol, can be used. Sodium amalgam and aluminum amalgam in aqueous-alcoholic or aqueous solutions are also suitable for producing the nascent hydrogen. The reaction can also be carried out in a heterogeneous phase, an aqueous phase and a benzene or toluene phase being preferably used. Suitable reaction temperatures include those between room temperature and the boiling point of the solvent.

Moreover, the phenoxy-amino-propanols of Formula I can be obtained by solvolysis or hydrogenolysis of a compound which has Formula I but which contains one or more group(s) which can be split off solvolytically or hydrogenolytically in place of one or more H atoms.

Suitable starting materials for this process variant include, in particular, compounds of the formula Ar—O—CH$_2$—CHOR$^5$—CH$_2$—NR$^2$R$^6$ (VII), wherein the radical R$^5$ is H or a hydroxyl protecting group and the radical R$^6$ is H or an amino protecting group; but the radicals R$^5$ and R$^6$ cannot simultaneously be H; and Ar and R$^2$ are as defined above.

The expressions "hydroxyl protecting group" and "amino protecting group" are well known and refer to groups which are suitable for protecting (blocking) a hydroxyl group or an amino group from chemical reactions but which can be easily removed after the desired chemical reaction has been carried out at other positions in the molecule. Since these protecting groups are later removed, their nature and size is in other respects not critical. However, R$^5$ and/or R$^6$ are preferably acyl with 1–20, in particular 1–8 C atoms (for example alkanoyl, such as acetyl; aroyl such as benzoyl; aralkanoyl, such as phenylacetyl; alkoxycarbonyl, such as methoxycarbonyl; aralkyloxycarbonyl, such as benzyloxycarbonyl; or arylsulphonyl, such as p-toluenesulphonyl); or optionally substituted benzyl (for example benzyl, p-nitrobenzyl or triphenylmethyl).

Solvolysis of these compounds is preferably effected by the action of a solvent such as water (hydrolysis) or of an alcohol with preferably 1–4 C atoms (alcoholysis) in the presence of an acidic or basic catalyst. Suitable such catalysts include mineral acids, such as sulphuric acid or hydrochloric acid; metal hydroxides, such as sodium, potassium, calcium, barium, lead or silver hydroxide; or metal or ammonium salts, such as sodium or potassium carbonate or ammonium chloride. Methanol, ethanol or isopropanol are preferably used as alcohols. Mixtures of water with one of these alcohols can also be used. The solvolysis is preferably carried out at temperatures between about 0° and about 120° C.

Hydrogenolysis can be carried out, for example, under the conditions described above for catalytic hydrogenation, preferably on a Raney nickel catalyst at temperatures between about 20° and 100° C. and under pressures between 1 and 10 atmospheres.

A base of Formula I can be converted into its associated acid addition salts by reaction with a suitable acid which produces a physiologically acceptable salt. Suitable salts include those of inorganic acids such as sulphuric acid, nitric acid, hydrogen halide acids, such as hydrochloric acid or hydrobromic acid, and phosphoric acid, such as orthophosphoric acid, and organic acids, in particular aliphatic, alicyclic, araliphatic, aromatic or heterocyclic monobasic or polybasic carboxylic or sulphonic acids, such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenyl-propionic acid, citric acid, gluconic acid, ascorbic acid, nicotinic acid, isonicotinic acid, methane- or ethane-sulphonic acid, ethanedisulphonic acid, 2-hydroxyethanesulphonic acid, benzenesulphonic acid, p-toluenesulphonic acid and naphthalene-mono- and di-sulphonic acids. If desired, the free bases of Formula I can be liberated from such salts by treatment with strong bases, such as sodium hydroxide or potassium hydroxide or sodium carbonate or potassium carbonate.

The compounds of Formula I are usually obtained in racemic form. When the compounds have two or more centers of asymmetry, they are generally obtained in synthesis as mixtures of racemates, from which the individual reacemates can be isolated and obtained in pure form, for example by several recrystallizations from suitable solvents.

The resulting racemates can be mechanically or chemically resolved into their optical antipodes by conventional methods. Preferably, diastereomers are formed from the racemic mixture by reaction with an optically active resolving agent. Suitable resolving agents are, for example, optically active acids, such as the D- and L- forms of tartaric acid, dibenzoyl tartaric acid, diacetyl tartaric acid, $\beta$-camphorsulphonic acid, mandelic acid, malic acid or latic acid. Furthermore, it is also possible to obtain optically active compounds by using starting materials which are already optically active in the foregoing preparative methods.

The compounds of Formula I possess very valuable pharmacological properties for mammals, including humans, and are well tolerated. They primarily exhibit isoprenaline-antagonism on the heart rate and blood pressure, for example in guinea pigs, cats or dogs. This effect can be determined, for example, by the method described in detail in German Auslegeschrift 1,493,564. Some of the compounds also exhibit a cardioselective action. Additionally, they can be used to lower cholesterol and triglyceride levels as can be determined in rats in accordance with the methods described by Levine and co-workers (Automation in Analytical Chemistry, Technicon Symposium, 1967, Mediad, New York, pages 25-28) and by Noble and Campbell (Clin. Chem. 16 (1970), pages 166-170). Furthermore, the products exert effects on the central nervous system; inhibit thrombocyte aggregation, display antiarrhythmic effects and inhibit lipolysis, all of which can be conventionally determined. The compounds thus exhibit a very broad spectrum of activity.

The compounds can accordingly be employed as medicaments in both human and veterinary medicine, in particular for the prophylaxis and treatment of cardiac, circulatory and vascular diseases, such as angina pectoris and coronary infarction as well as symptoms connected with these, e.g. hypertonia and arrhythmic effects.

The compounds are adrenergic $\beta$-receptor blockers similar to propranolol. In contrast to propranolol, however, they do not show strong undesired broncho constrictoric effects but are cardioselective $\beta_1$-blockers.

Furthermore, they can be used as intermediate products for the preparation of other medicaments.

The compounds of Formula I and their physiologically acceptable salts can be prepared for pharmaceutical use by formulation in a suitable dosage form together with at least one excipient or auxiliary and, if desired, together with one or more other active compound(s). The formulations thus obtained can be employed in human or veterinary medicine. Suitable excipients include conventional organic or inorganic substances used for enteral (for example oral) or parenteral administration or topical application which do not react with the new compounds. These include, for example, water, vegetable oils, benzyl alcohols, polyethylene glycols, glycerol triacetate, gelatin, carbohydrates, such as lactose or starch, magnesium stearate, talc or petroleum jelly. Tablets, dragees, capsules, syrups, elixirs, drops etc. can be used for oral administration; suppositories can be used for rectal administration; solutions, preferably oily or aqueous solutions, and also suspensions, emulsions or implantates can be used for parenteral administration; and ointments, creams or powders can be used for topical application. The new compounds can also be lyophilised and the resulting lyophilisates can be used, for example, for the preparation of injection formulations. All these formulations can be sterilized and/or can contain auxiliaries, such as lubricants, preservatives, stabilizers and/or wetting agents, emulsifiers, salts for influencing the osmotic pressure, buffer substances, dyestuffs, flavoring agents and/or aroma generating substances. If desired, they can also contain one or more other active compounds, for example one or more vitamins.

Generally, the compounds of this invention are administered in a manner analogous to that known for commercially available cardiac and circulatory formulations, in particular $\beta$-receptor blockers, preferably in dosages between about 0.5 and 200 mg, in particular between 2 and 50 mg, per dosage unit. The daily dosage is preferably between about 0.01 and 4 mg/kg of body weight. However, the specific dose suitable for an individual patient depends on the usual diverse factors, for example the activity of the specific compound employed, age, body weight, general state of health, sex, diet, time and method of administration, rate of excretion, medicament combination and severity of the particular disease for which therapy is given. Oral administration is preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

Each of the compounds of formula I mentioned in the examples is particularly suitable for the preparation of pharmaceutical formulations.

In the examples, the "customary work up" refers to the following procedure: water is added, if necessary; the mixture is extracted with an organic solvent, such as ethyl acetate, chloroform or dichloromethane, and separated; the organic phase is dried over sodium sulphate and filtered; the filtrate is evaporated; and the residue is purified by chromatography and/or cystallization.

A "fumarate" is the neutral salt produced from 2 moles of base and 1 mole of fumaric acid.

EXAMPLE 1

A mixture of 22 g. of crude oily 1-(p-allyloxymethyl-phenoxy)-2,3-epoxypropane [obtainable by heating p-hydroxybenzylalcohol with allyl alcohol to 150° for 4 hours and reacting the resulting p-allyloxymethyl-phenol (boiling point 123°–125°/0.01 mm. Hg) with epichlorohydrin] and 20 g. of 3,4-dimethoxyphenylethylamine was stirred for 12 hours at 25°. 60 ml. of ethanol were added to the resulting 1-(p-allyloxymethyl-phenoxy)-3-[2-(3,4-dimethoxyphenyl)-ethylamino]-propan-2-ol and the precipitate was filtered off and recrystallized from isopropanol. Hydrochloride, melting point 126°.

EXAMPLES 2 TO 27

Analogously to Example 1, reacting
1-(o-allyloxymethyl-phenoxy)-2,3-epoxypropane,
1-(m-allyloxymethyl-phenoxy)-2,3-epoxypropane,
1-(p-allyloxymethyl-phenoxy)-2,3-epoxypropane,
1-(o-propargyloxymethyl-phenoxy)-2,3-epoxypropane,
1-(o-2-methoxyethoxymethyl-phenoxy)-2,3-epoxypropane,
1-(o-2-isopropoxyethoxymethyl-phenoxy)2,3-epoxypropane,
1-(p-2-isopropoxyethoxymethyl-phenoxy)-2,3-epoxypropane,
1-(o-2-allyloxyethoxymethyl-phenoxy)-2,3-epoxypropane or
2-(o-cyclopentoxymethyl-phenoxy)-2,3-epoxypropane
(each obtainable from o-, m- or p-hydroxybenzyl alcohol by etherification with the corresponding alcohol and subsequent reaction with epichlorohydrin) with 2-phenylethylamine, 1,1-dimethyl-2-phenylethylamine or 2-(3,4-dimethoxyphenyl)-ethylamine produced:

2. 1-(o-Allyloxymethyl-phenoxy)-3-(2-phenylethylamino)-propan-2-ol, fumarate, m.p. 93°.
3. 1-(o-Allyloxymethyl-phenoxy)-3-(1,1-dimethyl-2-phenylethylamino)-propan-2-ol.
4. 1-(o-Allyloxymethyl-phenoxy)-3-[2-(3,4-dimethoxyphenyl)-ethylamino]-propan-2-ol, fumarate, m.p. 110°.
5. 1-(m-Allyloxymethyl-phenoxy)-(2-phenylethylamino)-propan-2-ol.
6. 1-(m-Allyloxymethyl-phenoxy)-(1,1-dimethyl-2-phenyl-ethylamino)-propan-2-ol.
7. 1-(m-Allyloxymethyl-phenoxy)-[2-(3,4-dimethoxyphenyl)-ethylamino]-propan-2-ol.
8. 1-(p-Allyloxymethyl-phenoxy)-3-(2-phenylethylamino)-propan-2-ol, hydrochloride, m.p. 150°.
9. 1-(p-Allyloxymethyl-phenoxy)-3-(1,1-dimethyl-2-phenylethylamino)-propan-2-ol, hydrochloride, m.p. 142°.
10. 1-(o-Propargyloxymethyl-phenoxy)-3-(2-phenylethylamino)-propan-2-ol, fumarate, m.p. 85°.
11. 1-(o-Propargyloxymethyl-phenoxy)-3-(1,1,-dimethyl-2-phenylethylamino)-propan-2-ol.
12. 1-(o-Propargyloxymethyl-phenoxy)-3-[2-(3,4-dimethoxyphenyl)-ethylamino]-propan-2-ol, fumarate, m.p. 115°.
13. 1-(o-2-Methoxyethoxymethyl-phenoxy)-3-(2-phenylethylamino)-propan-2-ol.
14. 1-(o-2-Methoxyethoxymethyl-phenoxy)-3-(1,1-dimethyl-2-phenylethylamino)-propan-2-ol.
15. 1-(o-2-Methoxyethoxymethyl-phenoxy)-3-[2-(3,4-dimethoxyphenyl)-ethylamino]-propan-2-ol.
16. 1-(o-2-Isopropoxyethoxymethyl-phenoxy)-3-(2-phenylethylamino)-propan-2-ol.
17. 1-(o-2-Isopropoxyethoxymethyl-phenoxy)-3-(1,1-dimethyl-2-phenylethylamino)-propan-2-ol.
18. 1-(o-2-Isopropoxyethoxymethyl-phenoxy)-3-[2-(3,4-dimethoxyphenyl)-ethylamino]-propan-2-ol, fumarate, m.p. 116°.
19. 1-(p-2-Isopropoxyethoxymethyl-phenoxy)-3-(2-phenylethylamino)-propan-2-ol.
20. 1-(p-2-Isopropoxyethoxymethyl-phenoxy)-3-(1,1-dimethyl-2-phenylethylamino)-propan-2-ol.
21. 1-(p-2-Isopropoxyethoxymethyl-phenoxy)-3-[2-(3,4-dimethoxyphenyl)-ethylamino]-propan-2-ol, hydrochloride, m.p. 126°.
22. 1-(o-2-Allyloxyethoxymethyl-phenoxy)-3-(2-phenylethylamino)-propan-2-ol.
23. 1-(o-2-Allyloxyethoxymethyl-phenoxy)-3-(1,1-dimethyl-2-phenylethylamino)-propan-2-ol, fumarate, m.p. 115°.
24. 1-(o-2-Allyloxyethoxymethyl-phenoxy)-3-[2-(3,4-dimethoxyphenyl)-ethylamino]-propan-2-ol, fumarate, m.p. 95°.
25. 1-(o-Cyclopentoxymethyl-phenoxy)-3-(2-phenylethylamino)-propan-2-ol.
26. 1-(o-Cyclopentoxymethyl-phenoxy)-3-(1,1-dimethyl-2-phenylethylamino)-propan-2-ol.
27. 1-(o-Cyclopentoxymethyl-phenoxy)-3-[2-(3,4-dimethoxyphenyl)-ethylamino]-propan-2-ol, hydrochloride, m.p. 127°.

EXAMPLE 28

A solution of 22 g. of 1-(o-allyloxymethyl-phenoxy)-2,3-epoxypropane and 33 ml. of isopropylamine in 45 ml. of ethanol was allowed to stand for 15 hours at 20°. The solution was evaporated and the residue dissolved in ethyl acetate and extracted with dilute hydrochloric acid. The aqueous phase was rendered alkaline and worked up in the customary manner. This produced 1-(o-allyloxymethyl-phenoxy)-3-isopropylamino-propan-2-ol; fumarate, m.p. 106°.

EXAMPLES 29 to 54

Analogously to Example 28, the epoxides indicated in Examples 2 to 27 and isopropylamine, tert.-butylamine or 1-methyl-2-hydroxyethylamine produced:

29. 1-(o-Allyloxymethyl-phenoxy)-3-tert.-butylamino-propan-2-ol.
30. 1-(o-Allyloxymethyl-phenoxy)-3-(1-methyl-2-hydroxyethylamino)-propan-2-ol.
31. 1-(m-Allyloxymethyl-phenoxy)-3-isopropylamino-propan-2-ol, fumarate, m.p. 90°.
32. 1-(m-Allyloxymethyl-phenoxy)-3-tert.-butylamino-propan-2-ol.
33. 1-(m-Allyloxymethyl-phenoxy)-3-(1-methyl-2-hydroxyethylamino)-propan-2-ol.
34. 1-(p-Allyloxymethyl-phenoxy)-3-isopropylamino-propan-2-ol, fumarate, m.p. 103°.
35. 1-(p-Allyloxymethyl-phenoxy)-3-tert.-butylamino-propan-2-ol, fumarate, m.p. 148°.
36. 1-(p-Allyloxymethyl-phenoxy)-3-(1-methyl-2-hydroxyethylamino)-propan-2-ol.
37. 1-(o-Propargyloxymethyl-phenoxy)-3-isopropylamino-propan-2-ol, fumarate, m.p. 177°.

38. 1-(o-Propargyloxymethyl-phenoxy)-3-tert.-butylamino-propan-2-ol, fumarate, m.p. 166°.

39. 1-(o-Propargyloxymethyl-phenoxy)-3-(1-methyl-2-hydroxyethylamino)-propan-2-ol.

40. 1-(o-2-Methoxyethoxymethyl-phenoxy)-3-isopropylamino-propan-2-ol, fumarate, m.p. 95°.

41. 1-(o-2-Methoxyethoxymethyl-phenoxy)-3-tert.-butylamino-propan-2-ol, fumarate, m.p. 115°.

42. 1-(o-2-Methoxyethoxymethyl-phenoxy)-3-(1-methyl-2-hydroxyethylamino)-propan-2-ol.

43. 1-(o-2-Isopropoxyethoxymethyl-phenoxy)-3-isopropylamino-propan-2-ol, fumarate, m.p. 90°.

44. 1-(o-2-Isopropoxyethoxymethyl-phenoxy)-3-tert.-butylamino-propan-2-ol, fumarate, m.p. 132°.

45. 1-(o-2-Isopropoxyethoxymethyl-phenoxy)-3-(1-methyl-2-hydroxyethylamino)-propan-2-ol.

46. 1-(p-2-Isopropoxyethoxymethyl-phenoxy)-3-isopropylamino-propan-2-ol, fumarate, m.p. 100°.

47. 1-(p-2-Isopropoxyethoxymethyl-phenoxy)-3-tert.-butylamino-propan-2-ol, hemifumarate, m.p. 105°.

48. 1-(p-2-Isopropoxyethoxymethyl-phenoxy)-3-(1-methyl-2-hydroxyethylamino)-propan-2-ol.

49. 1-(o-2-Allyloxyethoxymethyl-phenoxy)-3-isopropylamino-propan-2-ol, fumarate, m.p. 92°.

50. 1-(o-2-Allyloxyethoxymethyl-phenoxy)-3-tert.-butylamino-propan-2-ol, fumarate, m.p. 122°.

51. 1-(o-2-Allyloxyethoxymethyl-phenoxy)-3-(1-methyl-2-hydroxyethylamino)-propane-2-ol.

52. 1-(o-Cyclopentoxymethyl-phenoxy)-3-isopropylamino-propan-2-ol, hydrochloride, m.p. 124°.

53. 1-(o-Cyclopentoxymethyl-phenoxy)-3-tert.-butylamino-propan-2-ol, hydrochloride, m.p. 128°.

54. 1-(o-Cyclopentoxymethyl-phenoxy)-3-(1-methyl-2-hydroxy-ethylamino)-propan-2-ol.

EXAMPLES 55 TO 73

Analogously to Example 28, reacting 1-(o-2-methoxyethoxymethyl-phenoxy)-2,3-epoxypropane with the corresponding amines produced:

55. 1-(o-2-Methoxyethoxymethyl-phenoxy)-3-methylamino-propan-2-ol.

56. 1-(o-2-Methoxyethoxymethyl-phenoxy)-3-(2-hexylamino)-propane-2-ol.

57. 1-(o-2-Methoxyethoxymethyl-phenoxy)-3-(3-hydroxy-2-hexylamino)-propan-2-ol.

58. 1-(o-2-Methoxyethoxymethyl-phenoxy)-3-cyclopropylamino-propan-2-ol.

59. 1-(o-2-Methoxyethoxymethyl-phenoxy)-3-cyclopentylamino-propane-2-ol.

60. 1-(o-2-Methoxyethoxymethyl-phenoxy)-3-cyclohexylamino-propane-2-ol.

61. 1-(o-2-Methoxyethoxymethyl-phenoxy)-3-cyclooctylamino-propan-2-ol.

62. 1-(o-2-Methoxyethoxymethyl-phenoxy)-3-benzylamino-propan-2-ol.

63. 1-(o-2-Methoxyethoxymethyl-phenoxy)-3-(2-p-tolylethylamino)-propan-2-ol.

64. 1-(o-2-Methoxyethoxymethyl-phenoxy)-3-(1-methyl-3-phenyl-propylamino)-propan-2-ol.

65. 1-(o-2-Methoxyethoxymethyl-phenoxy)-3-(2-p-methoxy-phenylethylamino)-propan-2-ol.

66. 1-(o-2-Methoxyethoxymethyl-phenoxy)-3-[2-(3,4,5-trimethoxyphenyl)-ethylamino]-propan-2-ol.

67. 1-(o-2-Methoxyethoxymethyl-phenoxy)-3-(2-p-hydroxyphenyl-ethylamino)-propan-2-ol.

68. 1-(o-2-Methoxyethoxymethyl-phenoxy)-3-(2-p-fluorophenylethylamino)-propan-2-ol.

69. 1-(o-2-Methoxyethoxymethyl-phenoxy)-3-(2-p-chlorophenyl-ethylamino)-propan-2-ol.

70. 1-(o-2-Methoxyethoxymethyl-phenoxy)-3-[2-(3,4-methylenedioxyphenyl)-ethylamino]-propan-2-ol.

71. 1-(o-2-Methoxyethoxymethyl-phenoxy)-3-[2-(3-methoxy-4-hydroxyphenyl)-ethylamino]-propane-2-ol.

72. 1-(o-2-Methoxyethoxymethyl-phenoxy)-3-[1,1-dimethyl-2-(3,4-dimethoxyphenyl)-ethylamino]-propan-2-ol.

73. 1-(o-2-Methoxyethoxymethyl-phenoxy)-3-[1,1-dimethyl-4-(3,4,5-trimethoxyphenyl)-butylamino]-propan-2-ol.

EXAMPLE 74

A mixture of 25.7 g. of 1-chloro-3-(p-allyloxymethyl-phenoxy)-propan-2-ol and 50 g. of 2-(3,4-dimethoxyphenyl)ethylamine was heated to 100° for 18 hours, cooled and worked up in the customary manner. This produced 1-(p-allyloxy-methylphenoxy)-3-[2-(3,4-dimethoxyphenyl)-ethylamino]-propan-2-ol. Hydrochloride, m.p. 126°.

EXAMPLES 75 TO 83

Analogously to Example 74, reacting
1-chloro-3-(p-vinyloxymethyl-phenoxy)-propan-2-ol,
1-chloro-3-(p-2-hexen-1-yl-oxymethyl-phenoxy)-propan-2-ol,
1-chloro-3-(p-ethinyloxymethyl-phenoxy)-propan-2-ol,
1-chloro-3-(p-5-hexin-1-yl-oxymethyl-phenoxy)-propan-2-ol,
1-chloro-3-(p-2-butoxyethoxymethyl-phenoxy)-propan-2-ol,
1-chloro-3-(p-2-vinyloxyethoxymethyl-phenoxy)-propan-2-ol,
1-chloro-3-[p-2-(2-buten-1-yloxy)-ethoxymethyl-phenoxy]-propan-2-ol,
1-chloro-3-(p-cyclopropoxymethyl-phenoxy)-propan-2-ol or
1-chloro-3-(p-cyclohexyloxymethyl-phenoxy)-propan-2-ol with
2-(3,4-dimethoxyphenyl)-ethylamine produced:

75. 1-(p-Vinyloxymethylphenoxy)-3-[2-(3,4-dimethoxyphenyl)-ethylamino]-propan-2-ol.

76. 1-(p-2-Hexen-1-yloxymethyl-phenoxy)-3-[2-(3,4-dimethoxyphenyl)-ethylamino]-propan-2-ol.

77. 1-(p-Ethinyloxymethyl-phenoxy)-3-[2-(3,4-dimethoxyphenyl)-ethylamino]-propan-2-ol.

78. 1-(p-5-Hexin-1-yloxymethyl-phenoxy)-3-[2-(3,4-dimethoxyphenyl)-ethylamino]-propan-2-ol.

79. 1-(p-2-Butoxyethoxymethyl-phenoxy)-3-[2-(3,4-dimethoxyphenyl)-ethylamino]-propan-2-ol.

80. 1-(p-2-Vinyloxyethoxymethyl-phenoxy)-3-[2-(3,4-dimethoxyphenyl)-ethylamino]-propan-2-ol.

81. 1-[p-2-(2-Buten-1-yloxy)-ethoxymethyl-phenoxy]-3-[2-(3,4-dimethoxyphenyl)-ethylamino]-propan-2-ol.

82. 1-(p-Cyclopropoxymethyl-phenoxy)-3-[2-(3,4-dimethoxyphenyl)-ethylamino]-propan-2-ol.

83. 1-(p-Cyclohexyloxymethyl-phenoxy)-3-[2-(3,4-dimethoxyphenyl)-ethylamino]-propan-2-ol.

EXAMPLE 84

A mixture of 22.3 g. of 1-(p-allyloxymethyl-phenoxy)-3-amino-propan-2-ol [obtainable by reacting 1-(p-allyloxymethylphenoxy)-2,3-epoxypropane with $NH_3$], 13.8 g. of potassium carbonate, 27 g. of 2-(3,4-dimethoxyphenyl)-ethyl bromide and 100 ml. of n-butanol was boiled for 24 hours, with stirring. The mixture was filtered, the filtrate evaporated and the residue worked up in the customary manner to give 1-(p-allyloxymethyl-phenoxy)-3-[2-(3,4-dimethoxyphenyl)-ethylamino]-propan-2-ol, hydrochloride, m.p. 126°.

EXAMPLE 85

A mixture of 16.4 g. of p-allyloxymethyl-phenol, 27.4 g. of 1-chloro-3-[2-(3,4-dimethoxyphenyl)-ethylamino]-propan-2-ol [obtainable from epichlorohydrin and 2-(3,4-dimethoxyphenyl)-ethylamine], 8 g. of sodium hydroxide, 400 ml. of ethanol and 20 ml. of water was heated to 100° for 10 hours. The mixture was evaporated to dryness, the residue treated with dilute hydrochloric acid and ethyl acetate and separated and the aqueous phase rendered alkaline with sodium hydroxide solution and worked up in the customary manner to give 1-(p-allyloxymethylphenoxy)-3-[2-(3,4-dimethoxyphenyl)-ethylamino]-propan-2-ol, hydrochloride, m.p. 126°.

EXAMPLE 86

A mixture of 39.9 g. of 1-(p-allyloxymethyl-phenoxy)-3-[2-(3,4-dimethoxyphenyl)-ethylamino]-acetone (obtainable from p-allyloxymethylphenol and 1-bromo-3-[2-(3,4-dimethoxyphenyl)-ethylamino]-propan-2-one), 4g. of NaBH$_4$ and 2 l. of methanol was stirred at 25° for 3 hours. It was worked up in the customary manner to give 1-(p-allyloxymethyl-phenoxy)-3-[2-(3,4-dimethoxyphenyl)-ethylamino]-propan-2-ol, hydrochloride, m.p. 126°.

EXAMPLE 87

A solution of 42.8 g. of N-(2-hydroxy-3-o-cyclopentyloxymethyl-phenoxy-propyl)-3,4-dimethoxy-phenylacetamide [obtainable from 3,4-dimethoxy-phenylacetyl chloride and 1-(o-cyclopentyloxymethyl-phenoxy)-3-amino-propan-2-ol] in 600 ml. of THF was added dropwise to a suspension of 10 g. of LiAlH$_4$ in 500 ml. of absolute ether, with stirring. The mixture was subsequently boiled for 20 hours and worked up in the customary manner to give 1-(o-cyclopentyloxymethyl-phenoxy)-3-[2-(3,4-dimethoxyphenyl)-ethylamino]-propan-2-ol, hydrochloride, m.p. 127°.

EXAMPLE 88

A solution of 10 g. of 1-(p-2-isopropoxyethoxymethylphenoxy)-3-isopropylideneamino-propan-2-ol [obtainable by reacting 1-(p-2-isopropoxyethoxymethylphenoxy)-2,3-epoxypropane with ammonia to give 1-(p-2-isopropoxyethoxymethylphenoxy)-3-amino-propan-2-ol and subsequently reacting this with acetone] in 250 ml. of ethanol was hydrogenated on 0.5 g. of Raney nickel at 25° under 1 atmosphere of pressure until 1 equivalent of H$_2$ had been absorbed. The mixture was filtered and the filtrate evaporated to give 1-(p-2-isopropoxyethoxymethyl-phenoxy)-3-isopropylamino-propan-2-ol, fumarate, m.p. 100°.

EXAMPLE 89

10 g. of N-[2-hydroxy-3-(p-2-isopropoxyethoxymethylphenoxy)-propyl]-N-isopropyl-acetamide [obtainable by reacting Na p-(2-isopropoxyethoxymethyl)-phenolate with N-(2-hydroxy-3-bromo-propyl)-N-isopropyl-acetamide] were boiled for 4 hours with 250 ml. of 20% hydrochloride acid. The mixture was evaporated and worked up in the customary manner to give 1-(p-2-isopropoxyethoxymethyl-phenoxy)-3-isopropylamino-propan-2-ol, fumarate, m.p. 100°.

EXAMPLE 90

10 g. of 1-(o-2-methoxyethoxymethyl-phenoxy)-2-acetoxy-3-tert.-butylamino-propane [obtainable from Na o-(2-methoxyethoxymethyl)-phenolate and 1-bromo-2-acetoxy-3-tert.-butylaminopropane] were boiled for 2 hours with 250 ml. of 10% ethanolic NaOH. The mixture was evaporated and worked up in the customary manner to give 1-(o-2-methoxyethoxymethyl-phenoxy)-3-tert.-butylamino-propan-2-ol, fumarate, m.p. 115°.

The examples which follow relate to pharmaceutical formulations which contain amines of formula I or their acid addition salts:

EXAMPLE A: TABLETS

A mixture of 1 kg. of 1-(p-allyloxymethyl-phenoxy)-3-[2-(3,4-dimethoxyphenyl)-ethylamino]-propan-2-ol hydrochloride, 4 kg. of lactose, 1.2 kg. of potato starch, 0.2 kg. of talc and 0.1 kg. of magnesium stearate was pressed into tablets using conventional procedures in such a way that each tablet contained 10 mg. of active compound.

EXAMPLE B: DRAGEES

Tablets were pressed as in Example A and then conventionally coated with sucrose, potato starch, talc, tragacanth and a dyestuff.

EXAMPLE C: CAPSULES 2 kg. of 1-(o-2-Methoxyethoxymethyl-phenoxy)-3-tert.-butylamino-propan-2-ol fumarate were conventionally filled into hard gelatine capsules, so that each capsule contained 20 mg. of the active compound.

EXAMPLE D: AMPOULES

A solution of 1 kg. of 1-(o-allyloxymethyl-phenoxy)-3-[2-(3,4-dimethoxyphenyl)-ethylamino]-propan-2-ol fumarate in 30 l. of doubly distilled water was filtered sterile, filled into ampoules and lyophilized and sealed under sterile conditions. Each ampoule contained 1 mg. of active compound.

Tablets, dragees, capsules and ampoules which contain one or more of the remaining active compounds of the formula I and/or their physiologically acceptable acid addition salts can be obtained analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. Phenoxy-amino-propanols of the formula

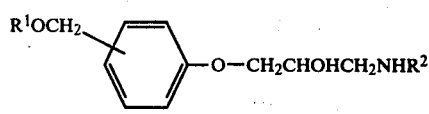

wherein $R^1$ is alkenyl, alkynyl, alkoxyalkyl, alkenyloxyalkyl, with 2–6 C atoms in each case, or cycloalkyl with 3–8 C atoms; and $R^2$ is aralkyl wherein the aryl radical is monosubstituted by methylenedioxy, with a total of 7–15 C atoms, and the physiologically acceptable acid addition salts thereof.

2. A pharmaceutical composition which comprises an amount of a compound of claim 1 effective for achieving isoprenaline-antagonism on the heart rate or blood pressure, and a pharmaceutically acceptable adjuvant.

3. A method of achieving isoprenaline-antagonism on the heart rate or blood pressure in a mammal, which comprises administering to a mammal an amount of a compound of claim 1 which is effective for achieving isoprenaline-antagonism on the heart rate or blood pressure.

4. 1-(o-2-Methoxyethoxymethyl-phenoxy)-3-[2-(3,4-methylenedioxyphenyl)-ethylamino]-propan-2-ol, a compound of claim 1.

5. A pharmaceutical composition which comprises an amount of a compound of claim 4 effective for achieving isoprenaline-antagonism on the heart rate or blood pressure, and a pharmaceutically acceptable adjuvant.

6. A method of achieving isoprenaline-antagonism on the heart rate or blood pressure in a mammal, which comprises administering to a mammal an amount of a compound of claim 4 which is effective for achieving isoprenaline-antagonism on the heart rate or blood pressure.

* * * * *